United States Patent
Li et al.

(10) Patent No.: US 10,054,487 B2
(45) Date of Patent: Aug. 21, 2018

(54) LAMINATED FILM AND FLEXIBLE ELECTRONIC DEVICE

(71) Applicant: SUMITOMO CHEMICAL COMPANY, LIMITED, Tokyo (JP)

(72) Inventors: Guan Li, Tsukuba (JP); Yasuhiro Yamashita, Tsukuba (JP); Mitsunori Nodono, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/508,823

(22) PCT Filed: Sep. 28, 2015

(86) PCT No.: PCT/JP2015/077240
§ 371 (c)(1),
(2) Date: Mar. 3, 2017

(87) PCT Pub. No.: WO2016/052369
PCT Pub. Date: Apr. 7, 2016

(65) Prior Publication Data
US 2017/0268929 A1    Sep. 21, 2017

(30) Foreign Application Priority Data

Sep. 30, 2014 (JP) ................................. 2014-199906

(51) Int. Cl.
*G01J 5/02* (2006.01)
*G01J 3/42* (2006.01)
(Continued)

(52) U.S. Cl.
CPC ................ *G01J 3/42* (2013.01); *B32B 15/08* (2013.01); *B32B 27/08* (2013.01); *B32B 27/281* (2013.01);
(Continued)

(58) Field of Classification Search
CPC .... G01J 3/42; G01J 3/73; G01N 21/31; G02F 1/1339; B32B 15/08; B32B 27/281
(Continued)

(56) References Cited

U.S. PATENT DOCUMENTS

| 9,011,994 B2 | 4/2015 | Hasegawa et al. |
| 2011/0197962 A1 | 8/2011 | Kawakami |

(Continued)

FOREIGN PATENT DOCUMENTS

| JP | 2003-335880 A | 11/2003 |
| JP | 2006-324406 A | 11/2005 |

(Continued)

OTHER PUBLICATIONS

International Search Report issued in PCT/JP2015/077240 (PCT/ISA/210), dated Dec. 15, 2015.
(Continued)

*Primary Examiner* — David Porta
*Assistant Examiner* — Meenakshi Sahu
(74) *Attorney, Agent, or Firm* — Birch, Stewart, Kolasch & Birch, LLP (57) ABSTRACT

An object of the present invention is to provide a gas barrier laminated film having high adhesion under a high-temperature working environment. The laminated film includes a flexible substrate, an organic layer disposed in contact with at least one surface of the substrate, and a thin film layer disposed in contact with the surface of the organic layer; the organic layer containing an acrylate resin; the thin film layer containing Si, O, and C; and the laminated film satisfying all of the following requirements (i) to (iii) in a silicon distribution curve, oxygen distribution curve, and carbon distribution curve in the thin film layer:

(i) the atomic number ratio of Si, the atomic number ratio of O, and the atomic number ratio of C satisfy the (Continued)

requirement represented by the following formula (1) in 90% or more of the area of the thin film layer in the film thickness direction of the thin film layer;

(Atomic number ratio of O)>(Atomic number ratio of Si)>(Atomic number ratio of C)

(ii) the carbon distribution curve has at least one extreme value; and (iii) the absolute value of a difference between the maximum value and the minimum value of the atomic number ratio of carbon in the carbon distribution curve is 0.05 or more.

9 Claims, 1 Drawing Sheet

(51) Int. Cl.
| | |
|---|---|
| G01N 21/73 | (2006.01) |
| G01N 21/31 | (2006.01) |
| B32B 38/00 | (2006.01) |
| G01N 21/35 | (2014.01) |
| B32B 27/08 | (2006.01) |
| H04M 1/02 | (2006.01) |
| G06F 1/16 | (2006.01) |
| G01N 25/72 | (2006.01) |
| B32B 27/28 | (2006.01) |
| G02F 1/1339 | (2006.01) |
| B32B 15/08 | (2006.01) |

(52) U.S. Cl.
CPC ......... *B32B 38/0008* (2013.01); *G01N 21/31* (2013.01); *G01N 21/35* (2013.01); *G01N 21/73* (2013.01); *G01N 25/72* (2013.01); *G02F 1/1339* (2013.01); *G06F 1/1652* (2013.01); *H04M 1/0268* (2013.01)

(58) Field of Classification Search
USPC ...................................................... 250/339.11
See application file for complete search history.

(56) References Cited

U.S. PATENT DOCUMENTS

| | | |
|---|---|---|
| 2012/0040107 A1 | 2/2012 | Hasegawa et al. |
| 2015/0044454 A1 | 2/2015 | Hasegawa |
| 2015/0291813 A1* | 10/2015 | Nishio ............... C23C 16/401 |
| | | 428/446 |

FOREIGN PATENT DOCUMENTS

| | | |
|---|---|---|
| JP | 2011-167882 A | 9/2011 |
| JP | 2013-71390 A | 4/2013 |
| JP | 2013-226767 A | 11/2013 |
| JP | 2014-195953 A | 10/2014 |
| WO | WO 2010/117046 A1 | 10/2010 |
| WO | WO 2013/146964 A1 | 10/2013 |
| WO | WO 2014/061627 A1 | 4/2014 |

OTHER PUBLICATIONS

Chinese Notification of the First Office Action and Search Report (including an English translation thereof) issued in the corresponding Chinese Patent Application No. 201580051842.2 dated Apr. 26, 2018.

* cited by examiner

LAMINATED FILM AND FLEXIBLE ELECTRONIC DEVICE

TECHNICAL FIELD

The present invention relates to a laminated film and a flexible electronic device.

BACKGROUND ART

Laminated films are known which are each provided with a thin film layer formed (laminated) on the surface of a substrate in order to impart functionality to a film-like substrate. For example, laminated films having gas barrier characteristics imparted by the formation of a thin film layer on a plastic film are suitable to the filling and packaging of products such as foods and drinks, cosmetics, and detergents. Plastic film substrates have been recently adopted in the fields of liquid crystal displays and organic EL elements to eliminate the drawbacks of glass substrates which are heavy, hard, and fragile. However, these plastic film substrates are inferior in gas barrier characteristics to glass substrates and there is therefore the case where steam penetrates into a device to cause display defects when the plastic film substrates are used in liquid crystal displays.

Methods for forming a thin film of an inorganic oxide on one surface of a substrate film such as a plastic film are being enthusiastically performed to solve this problem. Also, Patent Document 1 discloses a laminated film obtained by forming an organic layer containing, as its major component, an acrylate having a glass transition temperature of 10° C. (Comparative Example 2) to −68° C. (Example 4) on the surface of a substrate film and then by laminating an inorganic layer of silicon oxide (SiO) on the surface of the organic layer. It is reported that when such a structure is adopted, a laminated film can be provided which is resistant to deterioration in gas barrier characteristics even under high temperature and low temperature environments alternately repeated (90° C.-20 minutes and 40° C.-20 minutes).

PRIOR ART DOCUMENT

Patent Document

Patent Document 1: JP-2011-167882

SUMMARY OF THE INVENTION

Problems to be Solved by the Invention

However, the gas barrier laminated film disclosed in Patent Document 1 poses the problem that the adhesive force at the interface between the organic layer and the thin film layer is unnecessarily sufficient, so that the both layers are easily peeled from each other under a high-temperature working environment.

Under this situation, the present invention has been made and it is an object of the present invention to provide a gas barrier laminated film having high adhesion even under a high-temperature working environment.

Means for Solving the Problems

The present invention provides a laminated film comprising a flexible substrate, an organic layer disposed in contact with at least one surface of the substrate, and a thin film layer disposed in contact with a surface of the organic layer; the organic layer containing an acrylate resin; the thin film layer containing a silicon atom, an oxygen atom, and a carbon atom; and the laminated film satisfying all of the following requirements (i) to (iii) in a silicon distribution curve, oxygen distribution curve, and carbon distribution curve each indicating a relationship between a distance from a surface of the thin film layer in a film thickness direction of the thin film layer and ratios of silicon atoms (atomic number ratio of silicon), oxygen atoms (atomic number ratio of oxygen), and carbon atoms (atomic number ratio of carbon) to a total number of silicon atoms, oxygen atoms, and carbon atoms contained in the thin film layer at a position corresponding to the distance:

(i) the atomic number ratio of silicon, the atomic number ratio of oxygen, and the atomic number ratio of carbon satisfy a requirement represented by the following formula (1) in 90% or more of an area of the thin film layer in the film thickness direction of the thin film layer;

$$\text{(Atomic number ratio of oxygen)>(Atomic number ratio of silicon)>(Atomic number ratio of carbon)} \quad (1)$$

(ii) the carbon distribution curve has at least one extreme value; and (iii) an absolute value of a difference between a maximum value and a minimum value of the atomic number ratio of carbon in the carbon distribution curve is 0.05 or more.

In the laminated film of the present invention, a weight ratio of $W_1/W_0$ that is a ratio of a weight $W_1$ of the acrylate resin component to a weight $W_0$ calculated by excluding a weight of a filler component contained in the organic layer from a total weight of the organic layer is preferably in a range defined by the following formula (2):

$$0.60 \leq W_1/W_0 \leq 1.00 \quad (2).$$

In the laminated film of the present invention, a weight ratio of $W_2/W_0$ that is a ratio of a weight $W_2$ of the organic silicon compound component to the weight $W_0$ calculated by excluding the weight of the filler component contained in the organic layer from the total weight of the organic layer is preferably in a range defined by the following formula (3):

$$W_2/W_0 \leq 0.10 \quad (3).$$

In the laminated film of the present invention, a ratio of an intensity ($I_2$) of a peak at 1240 to 1290 $cm^{-1}$ to an intensity ($I_1$) of a peak at 950 to 1050 $cm^{-1}$ is preferably in a range defined by the following formula (4) when the surface of the thin film layer is subjected to infrared spectrometry:

$$0.01 \leq I_2/I_1 < 0.05 \quad (4).$$

In the laminated film of the present invention, a ratio of an intensity ($I_3$) of a peak at 770 to 830 $cm^{-1}$ to the intensity ($I_1$) of a peak at 950 to 1050 $cm^{-1}$ is preferably in a range defined by the following formula (5) when the surface of the thin film layer is subjected to infrared spectrometry:

$$0.25 \leq I_3/I_1 \leq 0.50 \quad (5).$$

In the laminated film of the present invention, a ratio of an intensity ($I_4$) of a peak at 870 to 910 $cm^{-1}$ to the intensity ($I_3$) of a peak at 770 to 830 $cm^{-1}$ is preferably in a range defined by the following formula (6) when the surface of the thin film layer is subjected to infrared spectrometry:

$$0.70 \leq I_4/I_3 < 1.00 \quad (6).$$

In the laminated film of the present invention, the thin film layer is preferably formed by a plasma CVD process.

The present invention also provides a flexible electronic device comprising the laminated film as a substrate.

EFFECT OF THE INVENTION

The present invention can provide a laminated film having high adhesion even under a high-temperature working environment. The laminated film of the present invention can be used as a substrate of a flexible electronic device and is industrially useful.

MODES FOR CARRYING OUT THE INVENTION

The modes for carrying out the present invention will be described hereinafter; however, the invention is not limited thereto.

[Laminated Film]

A laminated film according to the present invention includes a flexible substrate, an organic layer disposed in contact with at least one surface of the substrate, and a thin film layer disposed in contact with the surface of the organic layer, in which the thin film layer contains a silicon atom, an oxygen atom, and a carbon atom, and the organic layer contains an acrylate resin.

The laminated film of the present invention satisfies all of the following requirements (i) to (iii) in a silicon distribution curve, oxygen distribution curve, and carbon distribution curve each indicating a relationship between a distance from the surface of the thin film layer in the film thickness direction of the thin film layer and ratios of silicon atoms (atomic number ratio of silicon), oxygen atoms (atomic number ratio of oxygen), and carbon atoms (atomic number ratio of carbon) to the total number of silicon atoms, oxygen atoms, and carbon atoms contained in the thin film layer at a position corresponding to the distance:

(i) the atomic number ratio of silicon, the atomic number ratio of oxygen, and the atomic number ratio of carbon satisfy the requirement represented by the following formula (1) in 90% or more of an area of the thin film layer in the film thickness direction of the thin film layer;

(Atomic number ratio of oxygen)>(Atomic number ratio of silicon)>(Atomic number ratio of carbon)    (1)

(ii) the carbon distribution curve has at least one extreme value; and (iii) the absolute value of a difference between the maximum value and the minimum value of the atomic number ratio of carbon in the carbon distribution curve is 0.05 or more.

Here, "the absolute value of a difference between the maximum value and the minimum value of the atomic number ratio of carbon is 0.05 or more" in the requirement (iii) means that the difference expressed by percentage is 5% or more.

In this description, the laminated film has one organic layer formed on one of two surfaces of the flexible substrate and a thin film layer further formed on the organic layer. The laminated film may have an organic layer and a thin film layer formed not only on one surface of the flexible substrate but also on the other surface of the flexible substrate. Here, the layer means one formed by a single production method.

An example of a method for forming the organic layer on the surface of the flexible substrate in the present invention will be described hereinafter.

The organic layer is formed by a method involving the following step (1):

(1) a step of applying at least one organic substance selected from the group consisting of an acrylate resin, acrylate monomer, and acrylate oligomer onto the flexible substrate to obtain a coating film.

When the organic material contains an acrylate monomer or acrylate oligomer, the method preferably further involves the following step (2):

(2) a step of curing the coating film to obtain a cured film.

The coating film obtained in the step (1) may be the organic layer, or the cured film obtained in the step (2) may be the organic layer.

<Step (1)>

The flexible substrate has a film-like or sheet-like form and examples of the material of the flexible substrate include resins and composite materials containing resins.

Examples of the resin include polyethylene terephthalate (PET), polybutylene terephthalate (PBT), polyethylene naphthalate (PEN), acrylate, methacrylate, polycarbonate (PC), polyarylate, polyethylene (PE), polypropylene (PP), cyclic polyolefin (COP, COC), polyamide, aromatic polyamide, polystyrene, polyvinyl alcohol, a saponified product of an ethylene-vinyl acetate copolymer, polyacrylonitrile, polyacetal, polyimide, polyether imide, polyamideimide, polyether sulfide (PES), and polyether ether ketone.

Examples of the composite material containing resin include substrates of a silicone resin such as polydimethylsiloxane, substrates of an organic/inorganic hybrid resin such as polysilsesquioxane, glass composite substrates, and glass epoxy substrates.

The material of the flexible substrate may be only one type or combinations of two or more types.

Among these, PET, PBT, PEN, cyclic polyolefin, polyimide, aromatic polyamide, glass composite substrates, or glass epoxy substrates are preferable as the material of the flexible substrate from the viewpoint of high transparency and heat resistance and low coefficient of linear thermal expansion.

The flexible substrate is preferably colorless and transparent from the viewpoint of the possibilities of transmitting or absorbing light. More specifically, the total light transmittance of the flexible substrate is preferably 80% or more and more preferably 85% or more. Also, the haze value of the flexible substrate is preferably 5% or less, more preferably 3% or less, and even more preferably 1% or less.

The flexible substrate preferably has insulation properties and an electric resistance of $10^6$ Ωcm or more from the viewpoint of the possibility of using the flexible substrate as substrates for electronic devices and energy devices.

The thickness of the flexible substrate may be properly set in consideration of stable production of a laminated film. For example, the thickness of the flexible substrate is preferably 5 to 500 µm, more preferably 10 to 200 µm, and even more preferably 50 to 100 µm from the viewpoint of the possibility of conveying a film even under vacuum.

The surface of the flexible substrate may be subjected to surface treatments such as corona treatment, plasma treatment, electric glow discharge treatment, surface-roughing treatment, chemical treatment, and adhesion promotion treatment according to the need. Conventionally known methods may be appropriately used as specific methods for this surface treatment.

As the method for applying the organic material, any of wet coating methods such as a spin coating method, spray coating method, blade coating method, dip coating method, roller coating method, and round coating method, and dry coating methods such as a vapor deposition method may be utilized.

The organic material may be dissolved in a solvent when the organic material is applied. Examples of the solvent include nonpolar solvents such as xylene, hexane, and cyclohexane, aprotic polar solvents such as toluene, acetone, methyl ethyl ketone, methyl isobutyl ketone, DMAc, DMF, γ-butyrolactone, NMP, and DMSO, protic polar solvents such as methanol, ethanol, isopropanol, diacetone alcohol, and water, and halogen solvents such as chloroform, dichloromethane, and carbon tetrachloride.

The organic layer of the laminated film of the present invention contains an acrylate resin. The acrylate resin is preferably a photocurable resin. A photocurable resin is a resin that starts to be polymerized by, for example, ultraviolet rays or electron rays to undergo curing.

The organic layer may contain resins other than an acrylate resin to an extent that the effect is not adversely affected.

Specific examples of such resins include polyester resins, isocyanate resins, ethylene vinyl alcohol resins, vinyl-modified resins, epoxy resins, phenol resins, urea melamine resins, styrene resins, and alkyl titanate. These resins may be contained either singly or in combinations of two or more types.

The acrylate resin is preferably a resin containing, as its major component, a structural unit derived from an acrylic monomer having a (meth)acryloyl group. Here, "major component" means that the content of the component is 50% by mass or more, preferably 70% by mass or more, and even more preferably 90% by mass or more based on the mass of all components of the organic layer. Examples of the acrylate resin may include acrylate resins, urethane acrylate resins, polyester acrylate resins, epoxyacrylate resins, and polyol acrylate resins. The acrylate resin is preferably a UV-curable acrylate resin, UV-curable urethane acrylate resin, UV-curable polyester acrylate resin, UV-curable epoxyacrylate resin, or UV-curable polyol acrylate resin. Here, the (meth)acryloyl means an acrylate or methacrylate.

The acrylate resin is preferably such that the temperature at which the elastic modulus of the surface of the organic layer drops by 50% or more is 150° C. or more when a variation in the temperature of the surface of the organic layer is evaluated by a rigid-body pendulum type physical properties testing instrument.

The organic material may contain an inorganic oxide filler for the purpose of increasing surface hardness and controlling refractive index. Specific examples of the inorganic oxide filler include silica, zirconia, titania, and alumina. These fillers may be contained either singly or in combinations of two or more types.

The organic material may contain a photopolymerization initiator for the purpose of easily initiating photopolymerization. Examples of the photopolymerization initiator include benzophenone and its derivatives, benzyldimethylketals, α-hydroxyalkylphenones, hydroxyketones, and aminoalkylphenones. Specifically, Irgacure series (for example, Irgacure 651, Irgacure 754, and Irgacure 184), Darocure series (for example, Darocure TPO and Darocure 1173), and Quantacure PDO commercially available from Ciba Specialty Chemicals Inc., and Ezacure series (for example, Ezacure TZM and Ezacure TZT) commercially available from Sartomer may be used.

Additives other than the above acrylate resin and the like, filler, and photopolymerization initiator may be contained in the organic material to an extent that the performance of the laminated film of the present invention is not adversely affected. Examples of the additives include a leveling agent, viscosity regulator, antioxidant, bluing agent, dyes, UVA, and anti-blocking agent.

In the organic layer of the present invention, a weight ratio of $W_1/W_0$ that is a ratio of a weight $W_1$ of the acrylate resin component to a weight $W_0$ calculated by excluding the weight of a filler component contained in the organic layer from the total weight of the organic layer is preferably in the range defined by the following formula (1).

$$0.60 \leq W_1/W_0 \leq 1.00 \tag{1}$$

In the organic layer of the present invention, the weight ratio of $W_1/W_0$ is preferably in the range of $0.60 \leq W_1/W_0 \leq 1.00$, more preferably in the range of $0.60 \leq W_1/W_0 \leq 0.99$, more preferably in the range of $0.70 \leq W_1/W_0 \leq 0.98$, and even more preferably in the range of $0.80 \leq W_1/W_0 \leq 0.97$ from the viewpoint of improving adhesion to the thin film layer and sufficiently undergoing a polymerization reaction.

The organic layer may contain an organic silicon compound derived from, for example, a silane coupling agent as a surfactant.

A weight ratio of $W_2/W_0$ that is a ratio of a weight $W_2$ of the organic silicon compound component to the weight $W_0$ calculated by excluding the weight of a filler component contained in the organic layer from the total weight of the organic layer is preferably in the range defined by the following formula (2).

$$W_2/W_0 \leq 0.10 \tag{2}$$

In the organic layer of the present invention, the weight ratio of $W_2/W_0$ is preferably in the range of $W_2/W_0 \leq 0.10$, more preferably in the range of $W_2/W_0 \leq 0.08$, and even more preferably in the range of $W_2/W_0 \leq 0.05$ from the viewpoint of improving adhesion to the thin film layer and surface smoothness.

The film thickness of the organic layer is preferably 500 nm to 5 μm and more preferably 1 μm to 3 μm from the viewpoint of the uniformity of the film thickness of the organic layer and a decrease in defects such as cracks.

The organic layer of the present invention preferably has an average surface roughness of 0.1 to 5.0 nm on the side in contact with the thin film layer. This makes the thin film layer denser. Here, the average surface roughness can be measured using an atomic force microscope (AFM) and is, at this time, preferably measured in a visual field of 1 μm×1 μm.

The organic layer of the present invention is disposed as an intermediate layer between the substrate and the thin film layer. The organic layer may be a uniform layer where the organic layer occupies the entire intermediate layer, or a separate intermediate layer may be disposed between the organic layer and the substrate.

The organic layer has heat resistance to a temperature of preferably 150° C. or more, more preferably 160° C. or more, even more preferably 170° C. or more, and particularly preferably 180° C. or more, from the viewpoint of being capable of having resistance to a temperature applied during thin film layer formation. The heat resistance as used herein means a temperature at which high heat resistance is obtained when an evaluation is carried out according to the following method.

<Evaluation of Heat Resistance of Organic Layer>

Using two films each obtained by forming the organic layer on the flexible substrate, the organic layers are overlapped on each other to manufacture a laminate sample. The obtained laminate sample is sandwiched between glass substrates from both sides. After heated at a predetermined temperature for 2 hours, the overlapped two films are peeled from each other at the interface of the organic layers to evaluate the heat resistance of the organic layer regarding the degree of difficulty of peeling according to the following standard.

Evaluation Standard:
  Inferior heat resistance: the two films are stick to each other so that they are not peeled from each other, or they are peeled from each other with difficulty.
  Good heat resistance: the two films are peeled from each other without any change (in resistance and appearance).

<Step (2)>

An example of a method for curing the organic layer obtained in <Step (1)> includes light irradiation.

In the method of photopolymerization of the acrylic monomer, ultraviolet rays of a mercury lamp or LED lamp are usually preferable as the light to be applied. Because the polymerization of acrylates and methacrylates is hindered by oxygen in the air, it is preferable to lower the concentration or partial pressure of oxygen during polymerization. When the concentration of oxygen during polymerization is lowered by a nitrogen substitution method, the concentration of oxygen is preferably 2% or less and more preferably 0.5% or less.

The organic layer may be subjected to liquid washing treatment for cleaning the surface of the organic layer on the side on which the thin film layer is to be formed, because the adhesion of the organic layer to the thin film layer is improved. Examples of the liquid washing treatment include pure water washing treatment, ultra-pure water washing treatment, ultrasonic water washing treatment, scrub washing treatment, rinse-washing treatment, and two-fluid rinsing treatment.

The organic layer is preferably subjected to surface activation treatment for cleaning the surface of the organic layer on the side on which the thin film layer is to be formed, because the adhesion of the organic layer to the thin film layer is improved. Examples of the surface activation treatment include corona treatment, vacuum plasma treatment, atmospheric plasma treatment, UV ozone treatment, vacuum ultraviolet excimer lamp treatment, and flame treatment.

Next, a method for forming the thin film layer in the present invention will be described.

The above thin film layer contains a silicon atom, oxygen atom, and carbon atom from the viewpoint of high denseness and a reduction of defects such as small gaps and cracks. In this case, the major component of the thin film layer is preferably a compound represented by the general formula $SiO_\alpha C_\beta$. Here, "major component" means that the content of the component is 50% by mass or more, preferably 70% by mass or more, and more preferably 90% by mass or more based on the mass of all components of the material. In this general formula, $\alpha$ is selected from positive numbers less than 2 and $\beta$ is selected from positive numbers less than 2.

One or more of $\alpha$ and $\beta$ in the above general formula may be either constant or variable in the thickness direction of the thin film layer.

Furthermore, the thin film layer may contain elements other than a silicon atom, oxygen atom, and carbon atom, for example, one or more atoms of a hydrogen atom, nitrogen atom, boron atom, aluminum atom, phosphorus atom, sulfur atom, fluorine atom, and chlorine atom.

When the thin film layer contains a hydrogen atom besides a silicon atom, oxygen atom, and carbon atom, a compound represented by the general formula $SiO_\alpha C_\beta H_\gamma$ is preferably a major component of the thin film layer. Here, "major component" means that the content of the component is 50% by mass or more, preferably 70% by mass or more, and more preferably 90% by mass or more based on the mass of all components of the material. In this general formula, $\alpha$ is selected from positive numbers less than 2, $\beta$ is selected from positive numbers less than 2, and $\gamma$ is selected from positive numbers less than 6. One or more of $\alpha$, $\beta$, and $\gamma$ in the above general formula may be either constant or variable in the thickness direction of the thin film layer.

When the average atomic number ratio of a carbon atom (C) to a silicon atom (Si) in the thin film layer is represented by C/Si, the ratio is preferably in the range of 0.10<C/Si<0.50, more preferably in the range of 0.15<C/Si<0.45, even more preferably in the range of 0.20<C/Si<0.40, and particularly preferably in the range of 0.25<C/Si<0.35 from the viewpoint of high denseness and a reduction of defects such as small gaps and cracks.

When the average atomic number ratio of an oxygen atom (O) to a silicon atom (Si) in the thin film layer is represented by O/Si, the ratio is preferably in the following of 1.50<O/Si<1.90, more preferably in the range of 1.55<O/Si<1.85, even more preferably in the range of 1.60<O/Si<1.80, and particularly preferably in the range of 1.65<O/Si<1.75 from the viewpoint of high denseness and a reduction of defects such as small gaps and cracks.

In this case, the average atomic number ratios C/Si and O/Si can be calculated after depth profile measurement is made in the following conditions by X-ray photoelectron spectroscopy (XPS) and the average atom concentration of each atom in the thickness direction is determined from each distribution curve of a silicon atom, nitrogen atom, oxygen atom, and carbon atom.

<XPS Depth Profile Measurement>
  Etching ion species: Argon ($Ar^+$)
  Etching rate (conversion value in terms of $SiO_2$ thermal oxide film): 0.05 nm/sec
  Etching interval (conversion value in terms of $SiO_2$): 10 nm
  X-ray photoelectron spectroscopic apparatus: (Model name: "VG Theta Probe", manufactured by Thermo Fisher Scientific Inc.)
  X-rays to be irradiated: single crystal spectrum $AlK\alpha$
  X-ray, spot and size: 800×400 μm elliptic shape When the surface of the thin film layer is subjected to infrared spectrometry, an intensity ratio of an intensity ($I_2$) of a peak at 1240 to 1290 $cm^{-1}$ to an intensity ($I_1$) of a peak at 950 to 1050 $cm^{-1}$ is preferably in the range defined by the following formula (4):

$$0.01 \leq I_2/I_1 < 0.05 \qquad (4)$$

The peak intensity ratio $I_2/I_1$ calculated based on the infrared spectrometry is considered to represent the relative ratio of bonding Si—$CH_3$ to bonding Si—O—Si in the thin film layer. The above laminated film satisfying the formula (4)

tends to be superior in gas barrier characteristics and in impact resistance from the viewpoint of high denseness and a reduction of defects such as small gaps and cracks. With regard to the range of the peak intensity ratio $I_2/I_1$, the range of $0.01 \leq I_2/I_1 < 0.05$ is preferable and the range of $0.02 \leq I_2/I_1 < 0.04$ is more preferable from the viewpoint of keeping the laminated film high in denseness.

The infrared spectrometry of the thin film layer of the laminated film may be performed by a Fourier transform infrared spectrometer (FT/IR-460Plus, manufactured by JASCO Corporation) with ATR attachment (PIKE MIRacle) including a germanium crystal as a prism.

When the surface of the thin film layer is subjected to infrared spectrometry, an intensity ratio of an intensity ($I_3$) of a peak at 770 to 830 $cm^{-1}$ to the intensity ($I_1$) of a peak at 950 to 1050 $cm^{-1}$ is preferably in the range defined by the following formula (5):

$$0.25 \leq I_3/I_1 \leq 0.50 \tag{5}$$

The peak intensity ratio $I_3/I_1$ calculated based on the infrared spectrometry is considered to represent the relative ratio of bonding Si—C, Si—O, or the like to bonding Si—O—Si in the thin film layer. The above laminated film satisfying the formula (5) is considered to be superior in bending resistance and impact resistance because carbon is introduced thereinto, while keeping high denseness. With regard to the range of the peak intensity ratio $I_3/I_1$, the range of $0.25 \leq I_3/I_1 \leq 0.50$ is preferable and the range of $0.30 \leq I_3/I_1 \leq 0.45$ is more preferable from the viewpoint of keeping the balance between the denseness and the bending resistance of the laminated film.

When the surface of the thin film layer is subjected to infrared spectrometry, an intensity ratio of an intensity ($I_4$) of a peak at 870 to 910 $cm^{-1}$ to the intensity ($I_3$) of a peak at 770 to 830 $cm^{-1}$ is preferably in the range defined by the following formula (6):

$$0.70 \leq I_4/I_3 < 1.00 \tag{6}$$

The peak intensity ratio $I_4/I_3$ calculated based on the infrared spectrometry is considered to represent the ratio of a peak derived from bonding Si—C in the thin film layer. The above laminated film satisfying the formula (6) is considered to be superior in bending resistance and impact resistance because carbon is introduced thereinto, while keeping high denseness. With regard to the range of the peak intensity ratio $I_4/I_3$, the range of $0.70 \leq I_4/I_3 < 1.00$ is preferable and the range of $0.80 \leq I_4/I_3 < 0.95$ is more preferable from the viewpoint of keeping the balance between the denseness and the bending resistance of the laminated film.

The thin film layer is preferably formed by a plasma chemical vapor deposition method (plasma CVD process) as will be described later.

The thin film layer is preferably formed using glow discharge plasma.

The thickness of the thin film layer is preferably 5 to 3000 nm from the viewpoint of being hard to be broken when the laminated film is bent. When a thin film layer is formed by a plasma CVD process using glow discharge plasma as will be mentioned later, the thickness of the thin film layer is more preferably 10 to 2000 nm and even more preferably 100 to 1000 nm because the thin film layer is formed while discharging through the substrate.

The thin film layer provided in the laminated film used in this embodiment preferably has an average density as high as 1.8 $g/cm^3$ or more. The "average density" of the thin film layer in this description can be determined by calculating the weight of the thin film layer in the measured range from the atomic numbers of silicon, carbon, and oxygen determined by Rutherford Backscattering Spectroscopy (RBS) and from the atomic number of hydrogen determined by Hydrogen Forward scattering spectroscopy (HFS) and by dividing the weight by the volume (product of the area irradiated with ion beams and film thickness) of the thin film layer in the measured range.

The thin film layer has a density of 1.8 $g/cm^3$ or more, and therefore, the laminated film has a structure with high denseness and reduced in defects such as small gaps and cracks. When the thin film layer includes a silicon atom, oxygen atom, carbon atom, and hydrogen atom, the average density of the thin film layer is preferably less than 2.22 $g/cm^3$.

The laminated film of the present invention has high transparency, and therefore, the total light transmittance of the laminated film is preferably 80% or more and more preferably 85% or more. The total transmittance can be measured by a direct reading phase computer (Model: HGM-2DP) manufactured by Suga Test Instruments Co., Ltd.

In this embodiment, a curve is referred to as a silicon distribution curve which shows a relationship between a distance from the surface of the thin film layer in the film thickness direction of the thin film layer and an atomic ratio of a silicon atom at each distance. Here, the surface of the thin film layer indicates a plane to be the surface of the laminated film. Similarly, a curve is referred to as an oxygen distribution curve which shows a relationship between the distance from the surface of the thin film layer in the film thickness direction of the thin film layer and an atomic ratio of an oxygen atom at each distance. Additionally, a curve is referred to as a carbon distribution curve which shows a relationship between the distance from the surface of the thin film layer in the film thickness direction of the thin film layer and an atomic ratio of a carbon atom at each distance. The atomic ratios of a silicon atom, oxygen atom, and carbon atom mean a ratio of the number of silicon atoms, a ratio of the number of oxygen atoms, and a ratio of the number of carbon atoms, respectively.

The silicon distribution curve, oxygen distribution curve, and carbon distribution curve of the thin film layer satisfy the following requirements (i) to (iii):

(i) the atomic number ratio of silicon, the atomic number ratio of oxygen, and the atomic number ratio of carbon satisfy the requirement represented by the following formula (5) in 90% or more of the area of the thin film layer in the film thickness direction of the thin film layer;

$$\text{(Atomic number ratio of oxygen)} > \text{(Atomic number ratio of silicon)} > \text{(Atomic number ratio of carbon)} \tag{5}$$

(ii) the carbon distribution curve has at least one extreme value; and (iii) an absolute value of a difference between the maximum value and the minimum value of the atomic number ratio of carbon in the carbon distribution curve is 0.05 or more.

It is preferable that the carbon distribution curve of the thin film layer be substantially continuous. The phrase the carbon distribution curve is substantially continuous means that the carbon distribution curve does not include a part where the atomic ratio of carbon discontinuously varies. Specifically, when a distance from the surface of the thin film layer in the film thickness direction is x [nm] and the atomic ratio of carbon is C, it is preferable to satisfy the following formula.

$$|dC/dx| \leq 0.01$$

Also, the carbon distribution curve of the thin film layer has at least one extreme value. The extreme value stated here means the maximum value or the minimum value of the atomic ratio of each element to the distance from the surface of the thin film layer in the film thickness direction. The extreme value is a value of atomic ratio at a point where the atomic ratio of an element turns from increase to decrease or at a point where the atomic ratio of an element turns from decrease to increase when the distance from the surface of the thin film layer in the film thickness direction is changed. The extreme value can be determined, for example, based on atomic ratios measured at a plurality of measurement positions in the film thickness direction. The positions at which the atomic ratio is measured are so set that the interval in the film thickness direction is, for example, 20 nm or less. A position of an extreme value in the film thickness direction can be obtained by, for example, comparing measured results at three or more measurement positions different from one another based on a discrete data group including measured results at each measurement position and by determining a position where the measured result turns from increase to decrease or a position where the measured result turns from decrease to increase. A position of an extreme value can also be obtained by, for example, differentiating an approximate curve determined from the aforementioned discrete data group. When the length of a section where the atomic ratio is monotonically increased or decreased is, for example, 20 nm or more from the position of an extreme value, the absolute value of a difference between the extreme vale and the atomic ratio at a position moved by 20 nm in the film thickness direction from the position of an extreme value is, for example, 0.03 or more.

The thin film layer so formed as to satisfy the requirement that the carbon distribution curve has at least one extreme value as mentioned above is more reduced in an increase in the amount of gas transmittance before and after the thin film layer is bent as compared with the case where the above requirement is unsatisfied. In other words, when the above requirement is satisfied, an effect of suppressing deterioration in gas barrier characteristics caused by bending is obtained. When the thin film layer is so formed that the number of extreme values in the carbon distribution curve is two or more, an increase in the amount of gas transmittance is smaller than the case where the number of extreme values in the carbon distribution curve is one. Also, when the thin film layer is so formed that the number of extreme values in the carbon distribution curve is three or more, an increase in the amount of gas transmittance is smaller than the case where the number of extreme values in the carbon distribution curve is two. When the carbon distribution curve has two or more extreme values, an absolute value of a difference between the distance to a position of a first extreme value from the surface of the thin film layer in the film thickness direction and the distance to a position of a second extreme value neighboring to the first extreme value from the surface of the thin film layer in the film thickness direction is preferably in the range of 1 nm or more and 200 nm or less, and more preferably in the range of 1 nm or more and 100 nm or less.

Also, the absolute value of a difference between the maximum value and the minimum value of the atomic ratio of carbon in the carbon distribution curve of the thin film layer is 0.05 or more. The thin film layer so formed as to satisfy the above requirement is more reduced in an increase in the amount of gas transmittance before and after the thin film layer is bent as compared with the case where the above requirement is unsatisfied. In other words, when the above requirement is satisfied, an effect of suppressing deterioration in gas barrier characteristics caused by bending is obtained. When the absolute value of a difference between the maximum value and the minimum value of the atomic ratio of carbon is 0.06 or more, the above effect is increased and when this absolute value is 0.07 or more, the above effect is more increased.

There is a tendency that the gas barrier characteristics of the thin film layer are more improved with a decrease in the absolute value of a difference between the maximum value and the minimum value of the atomic ratio of silicon in the silicon distribution curve. From this point of view, the above absolute value is preferably less than 0.05 (less than 5 at %), more preferably less than 0.04 (less than 4 at %), and particularly preferably less than 0.03 (less than 3 at %).

Also, when the sum of the atomic ratios of an oxygen atom and a carbon atom at each distance in the oxygen-carbon distribution curve is defined as "total atomic ratio", there is a tendency that the gas barrier characteristics of the thin film layer are improved with a decrease in the absolute value of a difference between the maximum value and the minimum value of the total atomic ratio. From this point of view, the total atomic ratio is preferably less than 0.05, more preferably less than 0.04, and particularly preferably less than 0.03.

When the thin film layer is made to have substantially uniform composition in the thin film layer surface direction, the gas barrier characteristics of the thin film layer can be made to be uniform and improved. The phrase substantially uniform composition means that, in the oxygen distribution curve, carbon distribution curve, and oxygen-carbon distribution curve, the numbers of extreme values existing in each of the film thickness directions at optional two points on the surface of the thin film layer are equal to each other, and the absolute values of differences between the maximum value and the minimum value of the atomic ratio of carbon in each carbon distribution curve are equal to each other or are different by 0.05 or less from each other.

The thin film layer so formed as to satisfy the above requirement can exhibit the gas barrier characteristics required for, for example, flexible electronic devices including, for example, organic EL elements.

[Method for Producing Laminated Film]

The laminated film of the present invention can be produced by forming the thin film layer by a known vacuum film formation method such as a plasma CVD process using a glow discharge plasma. The generated plasma is high-density and low-temperature plasma and is therefore preferable because it is suitable to the formation of a dense and thin film on such a flexible substrate having low heat resistance as those used in the present invention.

When the thin film layer is formed (film formation) by a plasma CVD process, it is preferable to form the thin film layer by a plasma CVD process in which a flexible substrate is disposed on a pair of film formation electrodes to discharge electricity between the pair of film formation electrodes, thereby generating plasma. The pair of film formation electrodes may have a form of parallel plates or rolls. When discharging electricity between a pair of film formation rolls in this manner, it is preferable to alternately invert the polarities of the pair of film formation rolls.

When plasma is generated by a plasma CVD process, it is preferable to generate plasma discharge in a space between a plurality of film formation rolls and it is more preferable to generate plasma by using a pair of film formation rolls, disposing a substrate in each of the pair of film formation rolls and discharging electricity between the pair of film formation rolls. This process ensures that the surface part of the substrate existing on one film formation roll is subjected to film formation and the surface part of the substrate existing on the other film formation roll is also subjected to film formation at the same time during film formation. Therefore, not only the thin film layer can be efficiently formed but also the rate of film formation can be doubled. Also, it is preferable to form the thin film layer on the surface of the substrate by a roll-to-roll system from the viewpoint of productivity. The apparatus which can be used for producing the laminated film by the plasma CVD process preferably has a structure which is provided with at least one pair of film formation rolls and a plasma power source and which is capable of discharging electricity between the pair of film formation rolls.

Examples of the film formation apparatus to be applied to the roll-to-roll system plasma CVD process include apparatuses provided with a feed roll, conveying roll, film formation roll, conveying roll, and winding roll in order from the film formation upstream side (upstream side in the substrate-conveying direction), and also provided with a gas supply tube, plasma generation power source, and magnetic field-generating apparatus. Among them, at least the film formation roll, gas supply tube, and magnetic field-generating apparatus are disposed in a vacuum chamber in the formation of the thin film layer, and this vacuum chamber is connected to a vacuum pump. The pressure inside of the vacuum chamber is controlled by the action of the vacuum pump.

The film formation apparatus is preferably provided with a pair of film formation rolls as the film formation roll and is preferably further provided with a conveying roll between these film formation rolls. Then, the film formation apparatus is also preferable which is further equipped with magnetic field generating apparatuses inside of these film formation rolls wherein these magnetic field generating apparatuses are so installed that they are not changed in posture with the rotation of the film formation rolls.

When such a film formation apparatus is used, the substrate wound by the feed roll is conveyed from the feed roll to the film formation roll in the former stage (upstream side) via the conveying roll disposed at the most upstream side. Then, the laminated film provided with the thin film layer formed on the surface of the substrate is conveyed to the film formation roll in the latter stage (downstream side) from the film formation roll in the former stage via the conveying roll. Then, the laminated film obtained by further film formation to form the thin film layer is conveyed to the winding roll from the film formation roll in the latter stage via the conveying roll disposed on farther downstream side (most downstream side) and is wound around the winding roll.

In the aforementioned film formation apparatus, the pair of film formation rolls (the former stage and the latter stage) is so disposed as to face each other. Then, the axes of these film formation rolls are substantially parallel to each other and have substantially equal diameters. In such a film formation apparatus, a film is formed when the substrate is conveyed on the former film formation roll and when the laminated film is conveyed on the latter film formation roll. As the film formation apparatus, an apparatus described in, for example, JP-A-2011-73430 or the like is used.

The film formation apparatus can generate plasma in a space sandwiched between the pair of film formation rolls. The plasma generation power source is electrically connected with the electrodes in these film formation rolls and these electrodes are disposed so as to sandwich the above space.

The film formation apparatus can generate plasma by the power supplied to the electrodes from the plasma generation power source. As the plasma generation power source, known power sources or the like may be properly used. Examples of the power source include AC power sources capable of alternately inverting the polarities of the above two electrodes. The plasma generation power source is so set that the power to be supplied is set to, for example, 0.1 to 10 kW and AC frequency is set to, for example, 50 Hz to 100 MHz from the viewpoint of a possibility of efficient film formation. AC frequency set to 1 MHz to 100 MHz may be used from the viewpoint of improving raw material gas decomposition efficiency.

The magnetic field-generating apparatus disposed inside of the film formation roll can generate a magnetic field in the aforementioned space and may generate a magnetic field so as to change the magnetic flux density in the direction of conveyance on the film formation roll.

The gas supply tube has the capability of supplying the supply gas used to form the thin film layer to the aforementioned space. The supply gas contains a raw material gas for the thin film layer. The raw material gas supplied from the gas supply tube is decomposed by the plasma generated in the space to thereby form the film component of the thin film layer. The film component of the thin film layer is deposited on the substrate or laminated film conveyed on the pair of film formation roll.

For example, an organic silicon compound containing silicon may be used as the raw material gas. Examples of the organic silicon compound include hexamethyldisiloxane, 1,1,3,3-tetramethyldisiloxane, vinyltrimethylsilane, methyltrimethylsilane, hexamethyldisilane, methylsilane, dimethylsilane, trimethylsilane, diethylsilane, propylsilane, phenylsilane, vinyltriethoxysilane, vinyltrimethoxysilane, tetramethoxysilane, tetraethoxysilane, phenyltrimethoxysilane, methyltriethoxysilane, and octamethylcyclotetrasiloxane. Among these organic silicon compounds, hexamethyldisiloxane and 1,1,3,3-tetramethyldisiloxane are preferable from the viewpoint of handleability of the compound and gas barrier characteristics of a thin film layer to be obtained. Also, these organic silicon compounds may be used either singly or in combinations of two or more types.

Also, besides the above organic silicon compound, monosilane may be contained as the raw material gas and this raw material gas may be used as the silicon source of the barrier film.

The supply gas may contain a reaction gas besides the raw material gas. As the reaction gas, a gas which reacts with the raw material gas to form inorganic compounds such as oxides and nitrides may be appropriately selected prior to use. Examples of the reaction gas for forming oxides include oxygen and ozone. Also, examples of the reaction gas for forming nitrides include nitrogen and ammonia. These reaction gases may be used either singly or in combinations of two or more types. When, for example, an oxynitride is formed, a combination of a reaction gas for forming oxides and a reaction gas for forming nitrides may be used.

The supply gas may contain at least one of a carrier gas and a discharge gas. As the carrier gas, a gas that promotes the supply of the raw material gas into the vacuum chamber may be appropriately selected prior to use. As the discharge gas, a gas that promotes the generation of plasma discharge in the space may be appropriately selected prior to use. Examples of the carrier gas and discharge gas include rare gases such as helium gas, argon gas, neon gas, and xenon gas; and hydrogen gas. These carrier and discharge gases may be used either singly or in combinations of two or more types.

The following explanations are furnished taking, as an example, a case of producing a silicon-oxygen type thin film layer. The supply gas in this example contains hexamethyldisiloxane (organic silicon compound: HMDSO: $(CH_3)_6Si_2O$) as the raw material gas and oxygen ($O_2$) as the reaction gas.

In the plasma CVD process, silicon dioxide is formed by the reaction shown by the following formula (A) when hexamethyldisiloxane and the supply gas containing oxygen are reacted.

$$(CH_3)_6Si_2O + 12O_2 \rightarrow 6CO_2 + 9H_2O + 2SiO_2 \qquad (A)$$

The ratio of the amount of the reaction gas to the amount of the raw material gas in the supply gas is so set as not to be excessively higher than the ratio (stoichiometric ratio) stoichiometrically required to react the raw material gas completely. For example, in the reaction shown by the formula (A), the amount of oxygen stoichiometrically required to completely oxidize 1 mol of hexamethyldisiloxane is 12 mol. In other words, a uniform silicon dioxide film is formed as the thin film layer in theory when the supply gas contains 12 mol or more of oxygen based on 1 mol of hexamethyldisiloxane. However, there is, actually, the case where apart of the supply gas to be supplied does not contribute to the reaction. In light of this, a gas containing the reaction gas is usually supplied in a ratio higher than the stoichiometric ratio to completely react the raw material gas. Actually, the molar ratio (hereinafter referred to as "effective ratio") of the reaction gas for completely reacting with the raw material gas to the raw material gas can be found by experiments or the like. For example, there is the case where the molar amount (flow rate) of oxygen is made to be 20 times (as the effective ratio) the molar amount (flow rate) of raw material hexamethyldisiloxane to thereby completely oxidize hexamethyldisiloxane by the plasma CVD process. In light of this, the ratio of the amount of the reaction gas to the amount of the raw material gas in the supply gas may be less than the effective ratio (for example, 20), may be a stoichiometric ratio or less (for example, 12), or may be less than the stoichiometric ratio (for example, 10).

In this example, if the condition of the reaction is set to be the condition where the reaction gas is deficient such that the raw material gas cannot be completely reacted, carbon atoms and hydrogen atoms in incompletely oxidized hexamethylsiloxane are incorporated into the thin film layer. For example, in the above film formation apparatus, the thin film layer can be formed so as to satisfy the prescribed requirement by appropriately controlling one or more parameters such as the kind of the raw material gas, the ratio of the molar amount of the reaction gas to the molar amount of the raw material gas in the supply gas, power to be supplied to the electrodes, pressure in the vacuum chamber, each diameter of the pair of film formation rolls, and substrate conveying speed. In this case, one or more of the above parameters may be changed with time or may be changed spacially in a film formation area within a period during which the substrate passes through the film formation area facing the above space.

The power supplied to the electrodes can be properly controlled according to, for example, the kind of the raw material gas and pressure in the vacuum chamber and can be set to, for example, 0.1 to 10 kW. When the power is 0.1 kW or more, this heightens the effect of suppressing the occurrence of particles. Also, when the power is 10 kW or less, this heightens the effect of suppressing a flexible substrate from being damaged and wrinkled by the heat generated from the electrodes.

The pressure (degree of vacuum) in the vacuum chamber is arranged at the inside of the discharge port and can be properly controlled corresponding to the kind of the raw material gas and the like and may be set to, for example, 0.1 Pa to 50 Pa, preferably 0.2 Pa to 10 Pa, more preferably 0.3 Pa to 5 Pa, even more preferably 0.4 Pa to 2 Pa, and particularly preferably 0.5 Pa to 1.5 Pa. If the pressure is higher than this range, a colorless and transparent thin film layer is obtained because damages to the substrate are suppressed during the formation of the thin film layer; however, on the other hand, the density of the thin film layer is lowered, leading to deterioration in barrier characteristics. If the pressure is lower than this range, this causes damages to the substrate during the formation of the thin film layer and therefore poses the problem concerning coloring such as yellowing though this improves adhesion.

The conveying speed (line speed) of the flexible substrate is preferably equal to the conveying speed of the substrate when the substrate is made to be in contact with the conveying roll as described above, although it may be properly controlled corresponding to, for example, the kind of the raw material gas and pressure in the vacuum chamber.

The thin film layer is preferably formed by a continuous film formation process and is more preferably continuously formed on a long length substrate conveyed continuously.

The thin film layer can be further formed on the flexible substrate from above by inverting the feed roll and winding roll to convey the substrate in a reverse direction after it is formed while conveying the flexible substrate from the feed roll to the winding roll. This process can be appropriately changed according to desired targets of the number of laminations, film thickness, and conveying speed.

As mentioned above, the laminated film in the present invention can make optical characteristics, gas barrier characteristics, bending resistance, and adhesion compatible with one another by forming a colorless and transparent thin film having high optical characteristics on a thin film layer highly adhesive to a substrate. The present invention also provides a laminated film superior in adhesion and impact resistance when forming a further layer on the thin film layer. The laminated film in the present invention can be used in the fields of packages requiring gas barrier characteristics, such as those used in foodstuffs, industrial products, and medical supplies. Also, the laminated film of the present invention is preferably used for flexible substrates in liquid crystal displays, solar batteries, and electronic devices such as organic EL.

When the laminated film of the present invention is used as a flexible substrate of an electronic device, a device may be formed directly on the laminated film, or after a device is formed on a separate substrate, the laminated film is laminated on the device.

EXAMPLES

The present invention will be described in more detail by way of specific examples.

<Heat Resistance Evaluation 1 of Organic Layer>

Two films each obtained by forming an organic layer on a flexible substrate were used to manufacture a laminate sample with the organic layer surfaces overlapped on each other. The obtained laminate sample was sandwiched between glass plates, followed by heating at 180° C. for 2 hours. The overlapped two films were peeled from each other at the interface of the organic layers to measure the difficulty of peeling, thereby evaluating the heat resistance of the organic layer based on the following standard.

(Standard of Evaluation)

Inferior heat resistance: Two films are stick firmly to each other and are not peeled from each other or peeled from each other with difficulty.

Good heat resistance: Two films are peeled from each other without any change (resistance and appearance).

<Heat Resistance Evaluation 2 of Organic Layer>

An organic layer was formed on a flexible substrate to manufacture a laminate sample. The relative modulus of elasticity of this laminate sample was measured using a Rigid-body Pendulum Type Physical Properties Testing Instrument (RPT-3000 W, manufactured by R & D Co., Ltd.). The temperature of the laminate sample was raised to 160° C. from 25° C. at a temperature rise rate of 10° C./min to calculate the rate of reduction in modulus of elasticity between 150° C. and 25° C.

<Adhesion Measurement of Laminated Film>

(i) Six cuts reaching the base were formed at intervals of 1 mm on the test surface by using a box cutter to make 25 crosscuts, a cellophane tape (Sellotape (registered tradename) No. 405 (industrial use), adhesive power: 3.93 N/10 mm, manufactured by Nichiban Co., Ltd.) was strongly press-bonded against the crosscut part, and then, the end of the tape was stripped from the surface at an angle of 60° according to JIS K5600, to evaluate adhesion between the organic layer and the thin film layer based on the condition of breakage from the results of stripping.

(ii) Crosscuts were formed in the same manner as in the above Adhesion measurement (i), the sample was dipped in 100° C. hot water for 2 hours, followed by drying, and then, a cellophane tape (Sellotape (registered tradename) No. 405 (industrial use), adhesive power: 3.93 N/10 mm, manufactured by Nichiban Co., Ltd.) was strongly press-bonded against the crosscut part, and then, the end of the tape was stripped from the surface at an angle of 60°, to evaluate adhesion between the organic layer and the thin film layer based on the condition of breakage from the results of stripping.

In the measurement method for Adhesion measurement (i) and Adhesion measurement (ii), the number of crosscuts which were not visually observed among 25 crosscuts was counted and expressed as a percentage.

<Optical Characteristics of Laminated Film>

The total light transmittance of the laminated film was measured by a direct reading phase computer (Model: HGM-2DP) manufactured by Suga Test Instruments Co., Ltd. After background measurement was made in the condition free from a sample, the laminated film was set to a sample holder to perform measurement, thereby determining the total light transmittance.

<Gas Barrier Characteristics of Laminated Film>

The gas barrier characteristics of the laminated film were measured by a calcium corrosion method (method described in JP-A-2005-283561) under conditions of a temperature of 40° C. and a humidity of 90% RH to determine the moisture permeability of the laminated film.

<Film Thickness of Thin Film Layer>

A thin film layer was formed on a flexible substrate and a step difference between a non-film forming part and a film forming part was measured by SURFCORDER ET200 manufactured by Kosaka Laboratory Ltd. to determine the film thickness (T) of the thin film layer.

Example 1

Using a biaxially stretched polyethylene terephthalate film (Q65HA, manufactured by Teijin DuPont Films Japan Limited, thickness: 100 μm, both surfaces were treated to promote adhesion) as a substrate, a UV-curable acrylate monomer solution (product name: ARONIX UV-3701, manufactured by Toagosei Co., Ltd.) containing no filler was applied as an organic coating solution to one surface of the substrate by a wet coating method, followed by drying at 80° C. for 1 minute, and then, the coating layer was irradiated with UV-rays (SP-9, manufactured by USHIO INC.) at an integrated dose of 30 mJ/cm$^2$ to form an organic layer having a thickness of 2 μm. The ratio $W_1/W_0$ of the weight $W_1$ of an acrylate resin component contained in the obtained organic layer to the weight $W_0$ of the organic layer was 0.8, and the ratio $W_2/W_0$ of the weight $W_2$ of an organic silicon compound component contained in the organic layer to the weight $W_0$ of the organic layer was 0. It was confirmed that the obtained substrate/organic layer film 1 had heat resistance to a temperature of 180° C. or more by the measurement of Heat resistance evaluation 1, and it was also confirmed that the rate of reduction in modulus of elasticity was 1% by the measurement of Heat resistance evaluation 2.

The substrate (thickness: 102 μm, width: 700 mm) coated with the organic layer was installed on the feed roll in the vacuum chamber. After the pressure in the vacuum chamber was set to $1 \times 10^{-3}$ Pa or less, a thin film layer was formed on the organic layer with conveying the substrate at a constant speed of 0.6 m/minute. In a plasma CVD apparatus used to form the thin film layer, plasma is generated between the electrodes consisting of the pair of film formation rolls, and the substrate is conveyed so as to be in contact with the surfaces of the electrodes to form a thin film layer on the substrate. Also, in the electrodes consisting of the pair of film formation rolls, a magnet is disposed in the electrode such that a magnetic flux is increased on both of the electrode and the substrate, and plasma is restricted at a high density on the electrodes and substrate when the plasma is generated.

Figure 1:
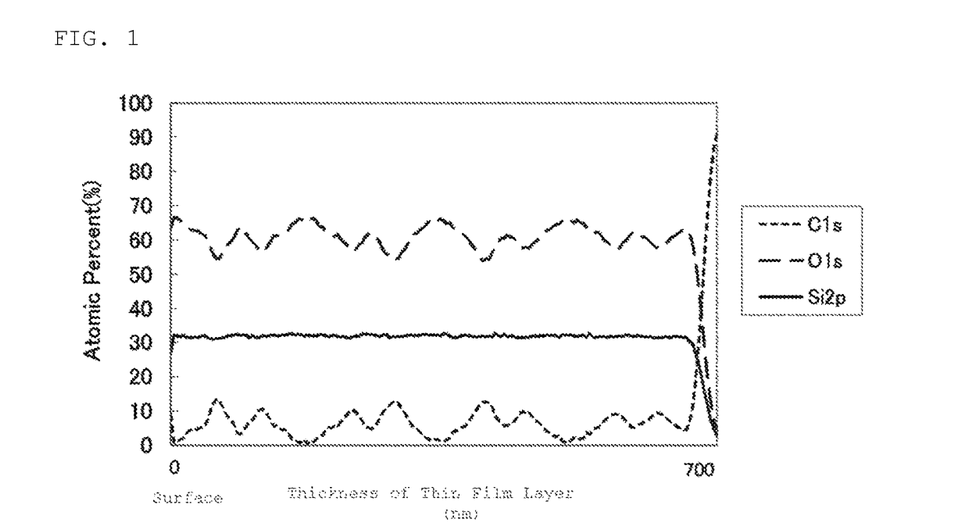
FIG. 1 is a graph illustrating a silicon distribution curve, oxygen distribution curve, nitrogen distribution curve, and carbon distribution curve of a thin film layer in a laminated film 1 obtained in Example 1.

In the formation of the thin film layer, 100 sccm (Standard Cubic Centimeter per Minute, 0° C., one atmosphere standard) of hexamethyldisiloxane gas and 900 sccm of oxygen gas were introduced toward a space to be a film formation zone between the electrodes, and an AC power of 1.6 kW with a frequency of 70 kHz was supplied to the electrode rolls to discharge electricity, thereby generating plasma. Then, exhaust volume was controlled such that pressure in the periphery of the exhaust port in the vacuum chamber was 1.0 Pa and then, a thin film layer was formed on the conveyed substrate by a plasma CVD process. With regard to the laminated film 1 obtained in this manner, the aforementioned adhesion measuring methods (i) and (ii) were performed, to find that the ratio of unpeeled places was 100% in each method, exhibiting good adhesion. The thickness of the thin film layer of the obtained laminate film 1 was 700 nm, the total light transmittance was 87%, and the moisture permeability was $3 \times 10^{-5}$ g/m$^2$/day. The silicon distribution curve, oxygen distribution curve, nitrogen distribution curve, and carbon distribution curve of the thin film layer in the laminated film 1 are illustrated in FIG. 1.

Also in the case of using a cyclic cycloolefin film (Zeonor ZF16, manufactured by ZEON Corporation, thickness: 100 μm, width: 700 mm) for subjecting only the thin film layer of the laminated film 1 to infrared spectrometry, a thin film layer was formed in the same operation to obtain a laminated film 1'. The thickness and structure of the thin film layer of the obtained laminated film 1' were the same as those of the laminated film 1. The obtained laminated film 1' was subjected to infrared spectrometry.

From the obtained infrared absorption spectrum, the absorption intensity ratio ($I_2/I_1$) of a peak intensity ($I_2$) at 1240 to 1290 cm$^{-1}$ to a peak intensity ($I_1$) at 950 to 1050 cm$^{-1}$ was determined to be $I_2/I_1$=0.03. Also, the absorption intensity ratio ($I_3/I_1$) of a peak intensity ($I_3$) at 770 to 830 cm$^{-1}$ to the peak intensity ($I_1$) at 950 to 1050 cm$^{-1}$ was determined to be $I_3/I_1$=0.37. Also, the absorption intensity ratio ($I_4/I_3$) of a peak intensity ($I_4$) at 870 to 910 cm$^{-1}$ to the peak intensity ($I_3$) at 770 to 830 cm$^{-1}$ was determined to be $I_4/I_3$=0.91.

Example 2

A substrate/organic layer film 2 and a laminated film 2 were obtained in the same manner as in Example 1 except that a UV-curable acrylate monomer solution (product name: LCH1559, manufactured by Toyo Ink Co., Ltd.) containing no filler was used as the organic coating solution. The ratio $W_1/W_0$ of the weight $W_1$ of an acrylate resin component contained in the obtained organic layer to the weight $W_0$ of the organic layer was 0.6, and the ratio $W_2/W_0$ of the weight $W_2$ of an organic silicon compound component contained in the organic layer to the weight $W_0$ of the organic layer was 0.

It was confirmed that the substrate/organic layer film 2 had heat resistance to a temperature of 180° C. or more by the measurement of Heat resistance evaluation 1, and it was also confirmed that the rate of reduction in modulus of elasticity was 0% by the measurement of Heat resistance evaluation 2. With regard to the obtained laminated film 2, the aforementioned adhesion measuring methods (i) and (ii) were performed, to find that the ratio of unpeeled places was 100% in each method, exhibiting good adhesion.

The thickness of the thin film layer of the obtained laminate film 2 was 700 nm, the total light transmittance was 87%, and the moisture permeability was $4\times10^{-5}$ g/m$^2$/day.

In the obtained laminated film 7, similarly to the laminated film 1 of Example 1, the order of the magnitudes of the atomic number ratios of oxygen, silicon, and carbon atoms is as follows in 90% or more of the area of the thin film layer in the film thickness direction of the thin film layer: (Atomic number ratio of oxygen)>(Atomic number ratio of silicon)>(Atomic number ratio of carbon), and the carbon distribution curve has one or more extreme values, and the absolute value of a difference between the maximum value and the minimum value of the atomic number ratio of carbon in the carbon distribution curve is 0.05 or more.

Example 3

A substrate/organic layer film 3 and a laminated film 3 were obtained in the same manner as in Example 1 except that a UV-curable urethane acrylate monomer solution (product name: BEAMSET 381, manufactured by Arakawa Chemical Industries Ltd.) containing no filler was used as the organic coating solution. The ratio $W_1/W_0$ of the weight $W_1$ of an acrylate resin component contained in the obtained organic layer to the weight $W_0$ of the organic layer was 0.7, and the ratio $W_2/W_0$ of the weight $W_2$ of an organic silicon compound component contained in the organic layer to the weight $W_0$ of the organic layer was 0. It was confirmed that the substrate/organic layer film 3 had heat resistance to a temperature of 180° C. or more by the measurement of Heat resistance evaluation 1, and it was also confirmed that the rate of reduction in modulus of elasticity was 0% by the measurement of Heat resistance evaluation 2. With regard to the obtained laminated film 3, the aforementioned adhesion measuring methods (i) and (ii) were performed, to find that the ratio of unpeeled places was 100% in each method, exhibiting good adhesion. The thickness of the thin film layer of the obtained laminate film 3 was 700 nm, the total light transmittance was 87%, and the moisture permeability was $5\times10^{-5}$ g/m$^2$/day.

In the obtained laminated film 3, similarly to the laminated film 1 of Example 1, the order of the magnitudes of the atomic number ratios of oxygen, silicon, and carbon atoms is as follows in 90% or more of the area of the thin film layer in the film thickness direction of the thin film layer: (Atomic number ratio of oxygen)>(Atomic number ratio of silicon)>(Atomic number ratio of carbon), and the carbon distribution curve has one or more extreme values, and the absolute value of a difference between the maximum value and the minimum value of the atomic number ratio of carbon in the carbon distribution curve is 0.05 or more.

Comparative Example 1

Using a biaxially stretched polyethylene terephthalate film (Q65HA, manufactured by Teijin DuPont Films Japan Limited, thickness: 100 µm, both surface were treated to promote adhesion) as a substrate, a thermosetting silicone resin solution (product name: TSR144, manufactured by Momentive Performance Materials Inc.) containing no filler was applied as an organic coating solution to one surface of the substrate by a wet coating method, followed by curing at 100° C. for 1 hour to form an organic layer having a thickness of 2 µm. The ratio $W_1/W_0$ of the weight $W_1$ of an acrylate resin component contained in the obtained organic layer to the weight $W_0$ of the organic layer was 0, and the ratio $W_2/W_0$ of the weight $W_2$ of an organic silicon compound component contained in the organic layer to the weight $W_0$ of the organic layer was 0.2. It was confirmed that the obtained substrate/organic layer film 4 had heat resistance to a temperature of 180° C. or more. Furthermore, a thin film layer was formed on the obtained substrate/organic layer film 4 in the same manner as in Example 1 to obtain a laminated film 4. On the other hand, with regard to the obtained laminated film 4, the aforementioned adhesion measuring method (i) was performed, to find that the ratio of unpeeled places was 80%, and also, the aforementioned adhesion measuring method (ii) was performed, to find that the ratio of unpeeled places was 20%, causing inferior adhesion.

Comparative Example 2

Using a thermosetting epoxy resin solution (product name: Conpoceran 103D, manufactured by Arakawa Chemical Industries Co., Ltd.) containing a filler as an organic coating solution, this solution was cured at 150° C. for 1 hour to form an organic layer having a thickness of 2 µm. The ratio $W_1/W_0$ of the weight $W_1$ of an acrylate resin component contained in the obtained organic layer to the weight $W_0$ calculated by excluding the weight of the filler component contained in the organic layer was 0, and the ratio $W_2/W_0$ of the weight $W_2$ of an organic silicon compound component contained in the organic layer to the weight $W_0$ calculated by excluding the weight of the filler component contained in the organic layer was 0. It was confirmed that the obtained substrate/organic layer film 5 had heat resistance to a temperature of 180° C. or more. Furthermore, a thin film layer was formed on the obtained substrate/organic layer film 5 in the same manner as in Example 1 to obtain a laminated film 5. On the other hand, with regard to the obtained laminated film 5, the aforementioned adhesion measuring method (i) was performed, to find that the ratio of unpeeled places was 100%, and also, the aforementioned adhesion measuring method (ii) was performed, to find that the ratio of unpeeled places was 16%, causing inferior adhesion.

Comparative Example 3

Figure 2:
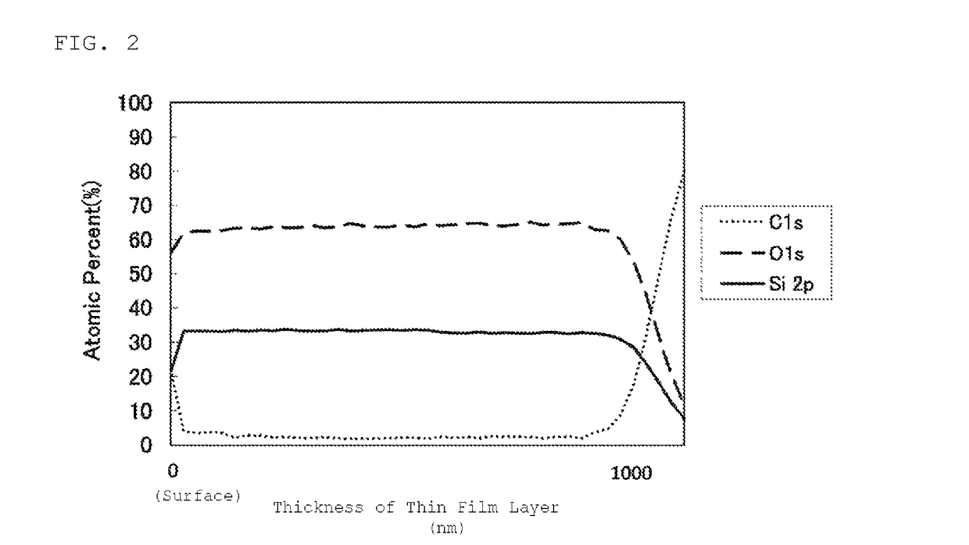
FIG. 2 is a graph illustrating a silicon distribution curve, oxygen distribution curve, nitrogen distribution curve, and carbon distribution curve of a thin film layer in a laminated film 6 obtained in Comparative Example 3.

A thin film layer was formed by an inductively coupled plasma CVD process using a glow discharge plasma on the substrate/organic layer film 1 obtained in Example 1. The inductively coupled CVD process is different from the aforementioned plasma CVD process and is a technique of generating plasma by applying high frequency power to an inductive coil to form an induced electric field. The biaxially stretched polyethylene naphthalate film used as the substrate had such an asymmetric structure that one surface thereof was treated to promote adhesion and the thin film layer was formed on the other surface untreated for promoting adhesion. In the film formation, 30 sccm (Standard Cubic Centimeter per Minute, 0° C., one atmosphere standard) of hexamethyldisiloxane gas, 150 sccm of oxygen gas, and 100 sccm of argon gas were introduced toward a film formation zone, and power of 0.9 kW with a frequency of 13.56 kHz was supplied to the inductive coil to discharge electricity, thereby generating plasma. Then, exhaust volume was controlled such that pressure in the vacuum chamber was 2.5 Pa and then, a thin film layer was formed on the conveyed substrate by an induced coupled plasma CVD process to obtain a laminated film 6. With regard to the laminated film 6 obtained in this manner, the aforementioned adhesion measuring methods (i) and (ii) were performed, to find that the ratio of unpeeled places was 100% in each method, exhibiting good adhesion. The thickness of the obtained laminate film 6 was 1000 nm, the total light transmittance was 90%, and the moisture permeability was 1.3 g/m²/day. The silicon distribution curve, oxygen distribution curve, nitrogen distribution curve, and carbon distribution curve of the thin film layer in the obtained laminated film 6 are illustrated in FIG. 2.

Example 4

A laminated film 7 was manufactured in the same manner as in Example 1 except that 100 sccm (Standard Cubic Centimeter per Minute, 0° C., one atmosphere standard) of hexamethyldisiloxane gas and 600 sccm of oxygen gas were introduced during the film formation of the thin film layer. The thickness of the thin film layer of the obtained laminate film 7 was 700 nm, the total light transmittance was 89%, and the moisture permeability was $4 \times 10^{-5}$ g/m²/day. With regard to the laminated film 7, the aforementioned adhesion measuring methods (i) and (ii) were performed, to find that the ratio of unpeeled places was 100% in each method, exhibiting good adhesion.

From the obtained infrared absorption spectrum, the absorption intensity ratio $(I_2/I_1)=0.03$. The absorption intensity ratio $(I_3/I_1)=0.42$. The absorption intensity ratio $(I_4/I_3)=0.90$.

In the obtained laminated film 7, similarly to the laminated film 1 of Example 1, the order of the magnitudes of the atomic number ratios of oxygen, silicon, and carbon atoms is as follows in 90% or more of the area of the thin film layer in the film thickness direction of the thin film layer: (Atomic number ratio of oxygen)>(Atomic number ratio of silicon)>(Atomic number ratio of carbon), and the carbon distribution curve has one or more extreme values, and the absolute value of a difference between the maximum value and the minimum value of the atomic number ratio of carbon in the carbon distribution curve is 0.05 or more.

Example 5

A laminated film 8 was manufactured in the same manner as in Example 1 except that 100 sccm (Standard Cubic Centimeter per Minute, 0° C., one atmosphere standard) of hexamethyldisiloxane gas and 800 sccm of oxygen gas were introduced during the film formation of the thin film layer. The thickness of the thin film layer of the obtained laminate film 8 was 700 nm, the total light transmittance was 88%, and the moisture permeability was $1 \times 10^{-5}$ g/m²/day. With regard to the laminated film 8, the aforementioned adhesion measuring methods (i) and (ii) were performed, to find that the ratio of unpeeled places was 100% in each method, exhibiting good adhesion.

From the obtained infrared absorption spectrum, the absorption intensity ratio $(I_2/I_1)=0.03$. The absorption intensity ratio $(I_3/I_1)=0.39$. The absorption intensity ratio $(I_4/I_3)=0.90$.

In the obtained laminated film 8, similarly to the laminated film 1 of Example 1, the order of the magnitudes of the atomic number ratios of oxygen, silicon, and carbon atoms is as follows in 90% or more of the area of the thin film layer in the film thickness direction of the thin film layer: (Atomic number ratio of oxygen)>(Atomic number ratio of silicon)>(Atomic number ratio of carbon), and the carbon distribution curve has one or more extreme values, and the absolute value of a difference between the maximum value and the minimum value of the atomic number ratio of carbon in the carbon distribution curve is 0.05 or more.

Example 6

A laminated film 9 was manufactured in the same manner as in Example 1 except that 100 sccm (Standard Cubic Centimeter per Minute, 0° C., one atmosphere standard) of hexamethyldisiloxane gas and 2000 sccm of oxygen gas were introduced during the film formation of the thin film layer. The thickness of the thin film layer of the obtained laminate film 9 was 700 nm, the total light transmittance was 88%, and the moisture permeability was $2 \times 10^{-5}$ g/m²/day. With regard to the laminated film 9, the aforementioned adhesion measuring methods (i) and (ii) were performed, to find that the ratio of unpeeled places was 100% in each method, exhibiting good adhesion.

From the obtained infrared absorption spectrum, the absorption intensity ratio $(I_2/I_1)=0.03$. The absorption intensity ratio $(I_3/I_1)=0.29$. The absorption intensity ratio $(I_4/I_3)=0.84$.

In the obtained laminated film 9, similarly to the laminated film 1 of Example 1, the order of the magnitudes of the atomic number ratios of oxygen, silicon, and carbon atoms is as follows in 90% or more of the area of the thin film layer in the film thickness direction of the thin film layer: (Atomic number ratio of oxygen)>(Atomic number ratio of silicon)>(Atomic number ratio of carbon), and the carbon distribution curve has one or more extreme values, and the absolute value of a difference between the maximum value and the minimum value of the atomic number ratio of carbon in the carbon distribution curve is 0.05 or more.

It was confirmed from the above results that the laminated film according to the present invention was superior in adhesion even in a high-temperature working environment.

It was also confirmed that the laminated film according to the present invention had high gas barrier characteristics and optical characteristics.

INDUSTRIAL APPLICABILITY

The present invention can be used for gas barrier films.

The invention claimed is:

1. A laminated film comprising a flexible substrate, an organic layer disposed in contact with at least one surface of the substrate, and a thin film layer disposed in contact with a surface side of the organic layer;

the organic layer containing an acrylate resin, and the organic layer having an average surface roughness of 0.1 to 5.0 nm on the surface side in contact with the thin film layer;

the thin film layer containing a silicon atom, an oxygen atom, and a carbon atom; and the laminated film satisfying all of the following requirements (i) to (iii) in a silicon distribution curve, oxygen distribution curve, and carbon distribution curve each indicating a relationship between a distance from a surface of the thin film layer in a film thickness direction of the thin film layer and ratios of silicon atoms (atomic number ratio of silicon), oxygen atoms (atomic number ratio of oxygen), and carbon atoms (atomic number ratio of carbon) to a total number of silicon atoms, oxygen atoms, and carbon atoms contained in the thin film layer at a position corresponding to the distance:

(i) the atomic number ratio of silicon, the atomic number ratio of oxygen, and the atomic number ratio of carbon satisfy a requirement represented by the following formula (1) in 90% or more of an area of the thin film layer in the film thickness direction of the thin film layer;

(Atomic number ratio of oxygen) >(Atomic number ratio of silicon) >(Atomic number ratio of carbon)    (1)

(ii) the carbon distribution curve has at least one extreme value; and (iii) an absolute value of a difference between a maximum value and a minimum value of the atomic number ratio of carbon in the carbon distribution curve is 0.05 or more.

2. The laminated film according to claim 1, wherein the organic layer may include a filler component, and a weight ratio of $W_1/W_0$ that is a ratio of a weight $W_1$ of the acrylate resin component to a weight $W_0$ calculated by excluding a weight of the filler component contained in the organic layer from a total weight of the organic layer is in a range defined by the following formula (2):

$$0.60 \leq W_1/W_0 \leq 1.00 \quad (2).$$

3. The laminated film according to claim 1, wherein a weight ratio of $W_2/W_0$ that is a ratio of a weight $W_2$ of the organic silicon compound component to the weight $W_0$ calculated by excluding the weight of the filler component contained in the organic layer from the total weight of the organic layer is in a range defined by the following formula (3):

$$W_2/W_0 \leq 0.10 \quad (3).$$

4. The laminated film according to claim 1, wherein an ratio of an intensity ($I_2$) of a peak at 1240 to 1290 cm$^{-1}$ to an intensity ($I_1$) of a peak at 950 to 1050 cm$^{-1}$ in a range defined by the following formula (4) when the surface of the thin film layer is subjected to infrared spectrometry:

$$0.01 \leq I_2/I_1 < 0.05 \quad (4).$$

5. The laminated film according to claim 1, wherein a ratio of an intensity ($I_3$) of a peak at 770 to 830 cm$^{-1}$ to the intensity ($I_1$) of a peak at 950 to 1050 cm$^{-1}$ is in a range defined by the following formula (5) when the surface of the thin film layer is subjected to infrared spectrometry:

$$0.25 \leq I_3/I_1 \leq 0.50 \quad (5).$$

6. The laminated film according to claim 1, wherein a ratio of an intensity ($I_4$) of a peak at 870 to 910 cm$^{-1}$ to the intensity ($I_3$) of a peak at 770 to 830 cm$^{-1}$ is in a range defined by the following formula (6) when the surface of the thin film layer is subjected to infrared spectrometry:

$$0.70 \leq I_4/I_3 < 1.00 \quad (6).$$

7. The laminated film according to claim 1, wherein the thin film layer is formed by a plasma CVD process.

8. A flexible electronic device comprising the laminated film according to claim 1 as a substrate.

9. The laminated film according to claim 1, wherein the thin film layer is formed by a plasma CVD process after the pressure in the vacuum chamber being set to $1 \times 10^{-3}$ Pa or less.

* * * * *